(12) United States Patent
Thompson et al.

(10) Patent No.: US 8,353,952 B2
(45) Date of Patent: Jan. 15, 2013

(54) STENT WITH THERAPEUTIC SUBSTANCE (75) Inventors: Dustin Thompson, Santa Rosa, CA (US); Paul Adler, Santa Rosa, CA (US); Maria Arreguin, Windsor, CA (US); Kevin Mauch, Windsor, CA (US); Christopher Storment, Sonoma, CA (US); Lance Ensign, Santa Rosa, CA (US); Stephen Zimmerman, Healdsburg, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 118 days.

(21) Appl. No.: 12/755,562

(22) Filed: Apr. 7, 2010

(65) Prior Publication Data

US 2011/0251668 A1  Oct. 13, 2011

(51) Int. Cl.
*A61F 2/82* (2006.01)
(52) U.S. Cl. ...................... 623/1.42; 623/1.15
(58) Field of Classification Search ......... 623/1.11–1.59
See application file for complete search history.

(56) References Cited

U.S. PATENT DOCUMENTS

| | | | |
|---|---|---|---|
| 6,004,346 A * | 12/1999 | Wolff et al. | 623/23.71 |
| 6,248,190 B1 | 6/2001 | Stinson | |
| 6,497,671 B2 | 12/2002 | Ferrera et al. | |
| 6,685,738 B2 | 2/2004 | Chouinard et al. | |
| 6,818,076 B1 * | 11/2004 | Farzin-Nia | 148/421 |
| 7,011,676 B2 | 3/2006 | Dong | |
| 7,896,899 B2 * | 3/2011 | Patterson et al. | 606/200 |
| 2001/0009982 A1 * | 7/2001 | Ferrera et al. | 600/585 |
| 2003/0208263 A1 | 11/2003 | Burmeister et al. | |
| 2004/0162606 A1 * | 8/2004 | Thompson | 623/1.22 |
| 2004/0250950 A1 | 12/2004 | Dubrow | |
| 2005/0038498 A1 | 2/2005 | Dubrow et al. | |
| 2007/0026132 A1 * | 2/2007 | Williams et al. | 427/2.25 |
| 2008/0021545 A1 | 1/2008 | Reneker et al. | |
| 2008/0103584 A1 * | 5/2008 | Su et al. | 623/1.16 |
| 2009/0192592 A1 * | 7/2009 | Asgari | 623/1.39 |
| 2009/0276029 A1 * | 11/2009 | Caro et al. | 623/1.11 |
| 2010/0030319 A1 * | 2/2010 | Weber | 623/1.11 |
| 2010/0198333 A1 * | 8/2010 | Macatangay et al. | 623/1.15 |
| 2010/0274350 A1 * | 10/2010 | Richter | 623/1.22 |
| 2012/0197384 A1 * | 8/2012 | Lee et al. | 623/1.15 |

FOREIGN PATENT DOCUMENTS

| | | |
|---|---|---|
| WO | WO 91/12779 | 9/1991 |
| WO | WO 99/29260 | 6/1999 |
| WO | WO 99/55256 | 11/1999 |

* cited by examiner

*Primary Examiner* — Suzette J Gherbi

(57) ABSTRACT

A stent includes a wave form that includes a cable including a plurality of strands. The wave form has a plurality of struts and a plurality of crowns, with each crown connecting two adjacent struts. The wave form is wrapped around a longitudinal axis at a pitch to define a plurality of helical turns. The stent includes a filler located within the cable. The filler includes a therapeutic substance.

5 Claims, 8 Drawing Sheets

STENT WITH THERAPEUTIC SUBSTANCE

BACKGROUND OF THE INVENTION

1. Field of the Invention

The present invention is related to a stent having a therapeutic substance for delivery to a target site in a body lumen and a method for manufacturing such a stent.

2. Background of the Invention

A wide range of medical treatments are known that utilize "endoluminal prostheses." As used herein, endoluminal prostheses are intended to mean medical devices that are adapted for temporary or permanent implantation within a body lumen, including both naturally occurring and artificially made lumens. Examples of lumens in which endoluminal prostheses may be implanted include, without limitation, arteries, such as those located within the coronary, mesentery, peripheral, or cerebral vasculature, veins, gastrointestinal tract, biliary tract, urethra, trachea, hepatic shunts, and fallopian tubes.

Various types of endoluminal prostheses are also known, each providing a structure for modifying the mechanics of the targeted luminal wall. For example, stent prostheses are known for implantation within body lumens for providing radial support to the wall tissue, which forms the various lumens within the body, and often more specifically within the blood vessels of the body.

To provide radial support to a blood vessel, such as one that has been widened by a percutaneous transluminal coronary angioplasty, commonly referred to as "angioplasty," "PTA" or "PTCA", a stent is implanted in conjunction with the procedure. Effectively, the stent is configured to overcome the natural tendency of the vessel walls of some patients to close back down (i.e. restenosis). As such, the stent acts as a scaffolding to resist the vessels tendency to close back down. Under this procedure, the stent may be collapsed to an insertion diameter and inserted into a body lumen at a site remote from the diseased vessel. The stent may then be delivered to the desired treatment site within the affected lumen and deployed, by self-expansion or balloon expansion, to its desired diameter for treatment.

In addition, it may be desirable to deliver a therapeutic substance to the treatment site in order to reduce the incidence of restenosis. Various drug eluting stents that simultaneously deliver a therapeutic substance to the treatment site while providing artificial radial support to the wall tissue are known. Therapeutic substances that may be delivered include antiplatelet agents, anticoagulant agents, antimicrobial agents, and antimetabolic agents. Endoluminal devices including stents are sometimes coated on their outer surfaces with a substance such as a drug releasing agent, growth factor, or the like. Stents have also been developed having a hollow tubular structure with holes or ports cut through the sidewall to allow drug elution from a central lumen, such as the stents disclosed in U.S. Pat. No. 5,891,108. Although the hollow nature of the stent allows the central lumen to be loaded with a drug solution that is delivered via the ports or holes in the sidewall of the stent, the hollow tubular structure may not have suitable mechanical strength to provide adequate scaffolding in the vessel.

SUMMARY OF THE INVENTION

It is desirable to have a drug eluting stent that can be tailored to provide a desired elution rate for one or more drugs and to provide sufficient quantities of one or more therapeutic substances without compromising the mechanics of the stent during deployment and use.

It is an aspect of the present invention to provide a stent that includes a wave form that includes a cable comprising a plurality of strands. The wave form has a plurality of struts and a plurality of crowns, with each crown connecting two adjacent struts. The wave form is wrapped around a longitudinal axis at a pitch to define a plurality of helical turns. The stent includes a filler located within the cable. The filler includes a therapeutic substance.

It is an aspect of the present invention to provide a method of manufacturing a stent. The method includes forming a cable that includes a plurality of strands, at least partially filling the cable with a filler that includes a therapeutic substance, forming a wave form having a plurality of struts and a plurality of crowns, with each crown connecting two adjacent struts, and wrapping the wave form about a longitudinal axis at a pitch to form a helical coil having a plurality of turns.

BRIEF DESCRIPTION OF THE DRAWINGS

Embodiments of the invention will now be described, by way of example only, with reference to the accompanying schematic drawings in which corresponding reference symbols indicate corresponding parts. The drawings are not to scale.

DETAILED DESCRIPTION OF EMBODIMENTS OF THE INVENTION

The following detailed description is merely exemplary in nature and is not intended to limit the invention or the application and use of the invention. Although the description of embodiments of the invention is in the context of treatment of blood vessels, such as periphery and coronary arteries, embodiments of the invention may also be used in any other body passageways where it is deemed useful. Furthermore, there is no intention to be bound by any expressed or implied theory presented in the preceding technical field, background, brief summary or the following detailed description.

Figure 1:
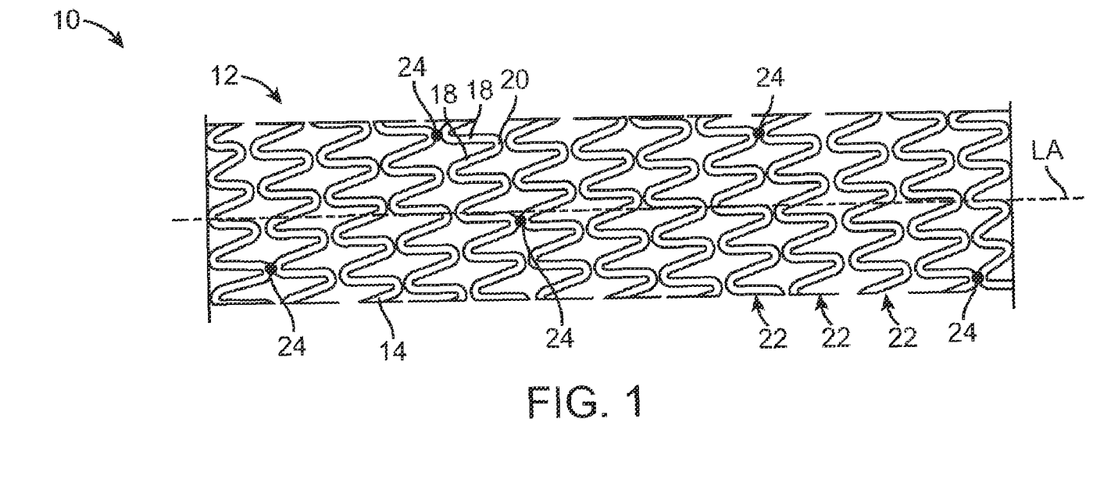
FIG. 1 schematically depicts a stent according to an embodiment of the present invention.

FIG. 1 schematically illustrates a stent 10 according to an embodiment of the present invention. The stent 10 is generally cylindrical in shape and has a longitudinal axis LA extending through the center of the stent 10. The stent 10 includes a continuous wave form 12 that is formed from a cable 14 having a plurality of strands (see, for example, FIG. 3), as discussed in further detail below.

Figure 2:
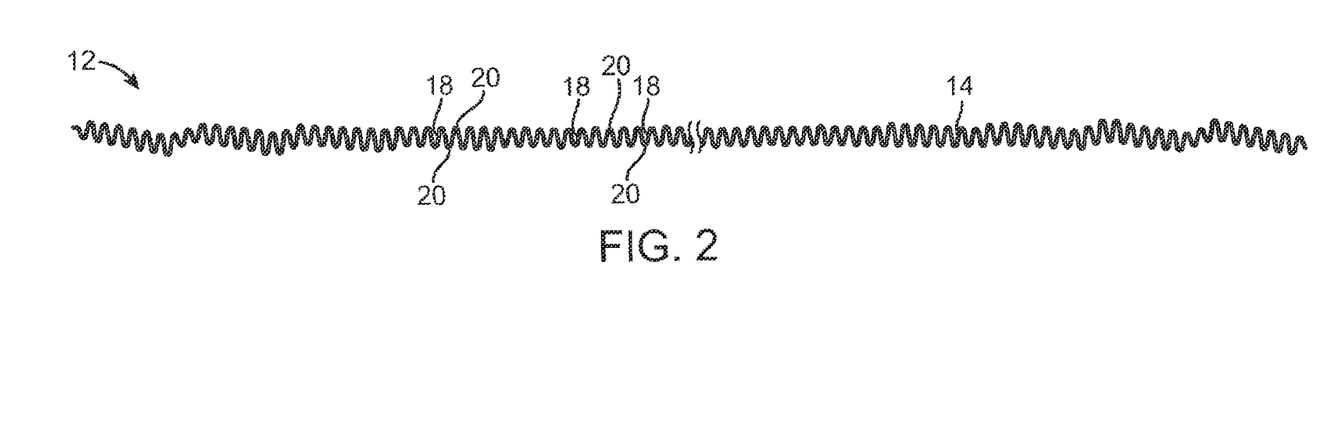
FIG. 2 schematically depicts a cable that has been formed into a wave form of the stent of FIG. 1.

As illustrated in FIG. 2, the wave form 12 may be formed so that the wave form 12 includes a plurality of struts 18 and a plurality of crowns 20. Each crown 20 is a curved portion or turn within the wave form 12 that connects adjacent struts 18 to define the continuous wave form 12. As shown in FIG. 2, the struts 18 are substantially straight portions of the wave form 12. In other embodiments, the struts 18 may be slightly bent or have other shapes, such as a sinusoidal wave, for example. The illustrated embodiment is not intended to be limiting in any way.

Figure 3:
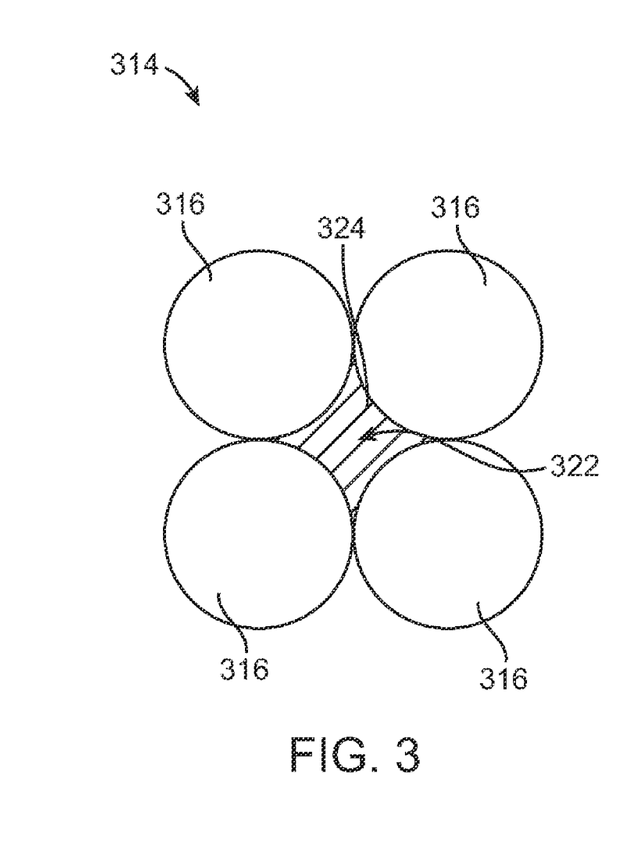
FIG. 3 schematically depicts a cross-section of an embodiment of the cable of FIG. 2.

FIG. 3 illustrates a cross-section of an embodiment of the cable 14, generally indicated at 314. As illustrated, the cable 314 includes four strands 316 of substantially the same diameter. In other embodiments, as little as three strands and as many as fifty or more strands may be used to form the cable 14. The illustrated embodiment is not intended to be limiting in any way.

The strands 316 may be formed from a wire or a strip of suitable material. Suitable materials for the strands include but are not limited to stainless steel, iridium, platinum, gold, tungsten, tantalum, palladium, silver, niobium, zirconium, aluminum, copper, indium, ruthenium, molybdenum, niobium, tin, cobalt, nickel, zinc, iron, gallium, manganese, chromium, titanium, aluminum, vanadium, and carbon, as well as combinations, alloys, and/or laminations thereof. For example, the strands may be formed from a cobalt alloy, such as L605, super elastic alloys such as MP35N® cobalt alloy, Nitinol (nickel-titanium shape memory alloy), ABI (palladium-silver alloy), Elgiloy® (cobalt-chromium-nickel alloy), etc.

It is also contemplated that the strands 316 may be formed from two or more materials that are laminated together, such as tantalum that is laminated with MP35N cobalt alloy. The strands may also be formed from wires having concentric layers of different metals, alloys, or other materials. Embodiments of the strands may also be formed from hollow tubes, or tubes that have been filled with other materials. The aforementioned materials and laminations are intended to be examples and are not intended to be limiting in any way. In an embodiment, all of the strands 316 within the cable 314 may be made from the same material. In an embodiment, different strands with the cable 314 may be made from different materials, as discussed in further detail below.

As illustrated in FIG. 3, the strands 316 are arranged so as to form a central cavity 322 therebetween. The central cavity 322 is configured to be at least partially filled with a filler 324 that may enter into the central cavity 322 after the central cavity 322 has been formed. In an embodiment, the filler 324 may be formed into a strand around which the strands 316 are subsequently wrapped. The filler 324 may include an elutable therapeutic substance or drug that may comprise a biologically or pharmacologically active substance.

The term "biologically or pharmacologically active substance" refers to any substance, whether synthetic or natural, that has a pharmacological, chemical, or biological effect on the body or a portion thereof. Suitable biologically or pharmacologically active materials that can be used in embodiments of the present invention include without limitation glucocorticoids (e.g. dexamethasone, betamethasone), anti-thrombotic agents such as heparin, cell growth inhibitors, hirudin, angiopeptin, aspirin, growth factors such as VEGF, antisense agents, anti-cancer agents, anti-proliferative agents, oligonucleotides, antibiotics, and, more generally, antiplatelet agents, anti-coagulant agents, antimitotic agents, antioxidants, antimetabolite agents, and anti-inflammatory agents may be used. Antiplatelet agents can include drugs such as aspirin and dipyridamole. Aspirin is classified as an analgesic, antipyretic, anti-inflammatory and antiplatelet drug. Dipyridamole is a drug similar to aspirin in that it has anti-platelet characteristics. Dipyridamole is also classified as a coronary vasodilator. Anticoagulant agents may include drugs such as heparin, protamine, hirudin and tick anticoagulant protein. Anti-cancer agents may include drugs such as taxol and its analogs or derivatives, such as paclitaxel. Taxol is also classified as a cell-growth inhibitor. Antioxidant agents may include probucol. Anti-proliferative agents may include drugs such as amlodipine, doxazosin, sirolimus, and zotarolimus or other—limus family compounds. Antimitotic agents and antimetabolite agents may include drugs such as methotrexate, azathioprine, vincristine, vinblastine, 5-fluorouracil, adriamycin and mutamycin. Antibiotic agents can include penicillin, cefoxitin, oxacillin, tobramycin, and gentamicin. Suitable antioxidants include probucol. Also, genes or nucleic acids, or portions thereof may be used. Such genes or nucleic acids can first be packaged in liposomes or nanoparticles. Furthermore, collagen-synthesis inhibitors, such as tranilast, may be used.

In an embodiment, the biologically or pharmacologically active substance may be suspended in a polymer matrix or carrier to prevent premature elution of the active therapeutic substance from the central cavity 322 until the stent 10 has been implanted at the treatment site. In an embodiment, the polymer matrix or carrier may be biodegradable or bioresorbable such that it is absorbed in the body. The polymer may be a single polymer, a copolymer blend, a polymer mixture, a copolymer mixture, or a polymer-copolymer mixture. The polymer can be a biostable polymer, a bioabsorbable polymer, or a biomolecular polymer. Suitable biostable or bioabsorbable polymers can be poly(L-lactic acid), polycaprolactone, poly(lactide-co-glycolide), poly(hydroxybutyrate), poly(hydroxybutyrate-covalerate), polydioxanone, polyorthoester, polyanhydride, poly(glycolic acid), poly(D,L-lactic acid), poly(glycolic acid-co-trimethylene carbonate), polyphosphoester, polyphosphoester urethane, poly(amino acids), cyanoacrylates, poly(trimethylene carbonate), poly (iminocarbonate), copoly(ether-esters) (e.g., polyethylene oxide (PEO), polylactic acid (PLA)), polyalkylene oxalates, polyphosphazenes. Suitable biomolecular polymers can be fibrin, fibrinogen, cellulose, starch, collagen or hyaluronic acid.

Other suitable polymers can be polyurethanes, silicones, polyesters, polyolefins, polyisobutylene and ethylene-alpha-olefin copolymers; acrylic polymers and copolymers, vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile, polyvinyl ketones; polyvinyl aromatics, such as polystyrene, polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as nylon 66 and polycaprolactam; alkyd resins; polycarbonates; polyoxymethylenes; polyimides; polyethers; epoxy resins;

polyurethanes; rayon; rayon-triacetate; cellulose, cellulose acetate, cellulose butyrate; cellulose acetate butyrate; cellophane; cellulose nitrate; cellulose propionate; cellulose ethers; and carboxymethyl cellulose. Those skilled in the art will recognize that various polymers and polymer mixtures are suitable for particular applications, depending on the desired elasticity and ability to carry the particular therapeutic agents.

In an embodiment, the filler 324 may be pre-loaded into the central cavity 322 prior to implantation of the stent 10 into a body lumen, with a proximal end and a distal end of the cable 314 being closed once the filler 324 is loaded within the central cavity 322. By "pre-loaded" it is meant that the therapeutic substance or drug may be filled or otherwise provided within the central cavity 322 of the cable 314. Once loaded, both the proximal end and the distal end of the cable 314 may be sealed or plugged prior to delivery into the body lumen. The proximal end and the distal end may be sealed with a plug (not shown), such as a plug of silicone. As previously described, the therapeutic substance may be suspended in an optionally biodegradable polymer matrix or carrier to prevent premature elution of the active therapeutic substance from the central cavity 322 until the stent 10 has been deployed at the treatment site. Once positioned inside of the body lumen at the desired location, the stent 10 may be deployed for permanent implantation in the body lumen such that the therapeutic substance may elute from the central cavity 322.

In addition, a readily dissolvable coating (not shown) may be utilized in embodiments of the present invention in order to prevent premature elution of the active therapeutic substance from the central cavity 322 until the stent 10 has been deployed at the treatment site. The coating may cover the outside surface of the cable 314 so as to fill in gaps between the strands 316, in a similar manner illustrated in FIGS. 10 and 11, discussed below. The coating may be a dextran type or any other appropriate coating that would dissolve very quickly, yet protect the therapeutic substance or drug as it is being delivered to the stenotic site of the body lumen. For example, coating materials that are sufficient to provide the desired short duration protection, such as polysaccharides including mannitol, sorbitol, sucrose, xylitol, anionic hydrated polysaccharides such as gellan, curdlan, XM-6, xanthan, are listed in U.S. Pat. No. 6,391,033. These materials dissolve in approximately ten to fifteen minutes in order to allow for proper stent placement at the target site.

Figure 4:
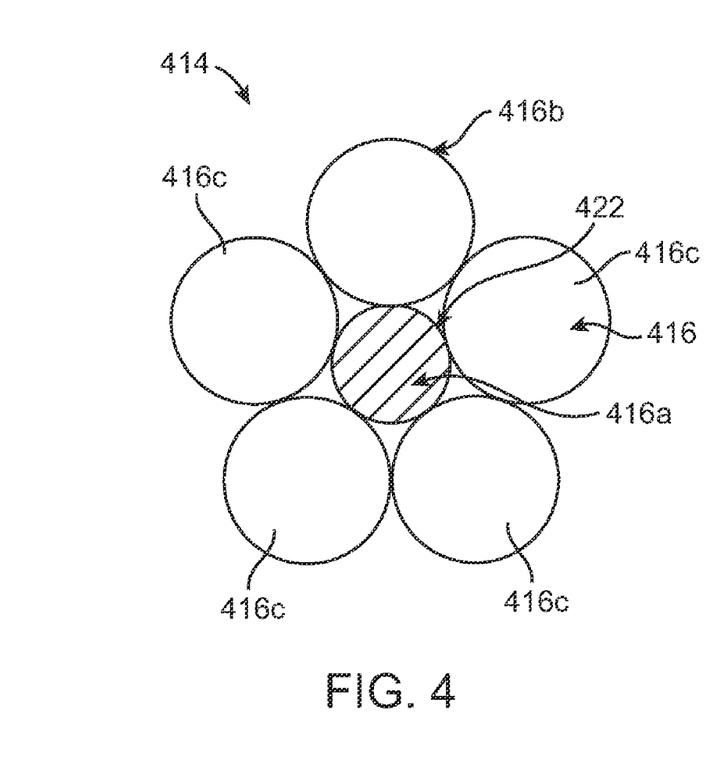
FIG. 4 schematically depicts a cross-section of an embodiment of the cable of FIG. 2.
Figure 5:
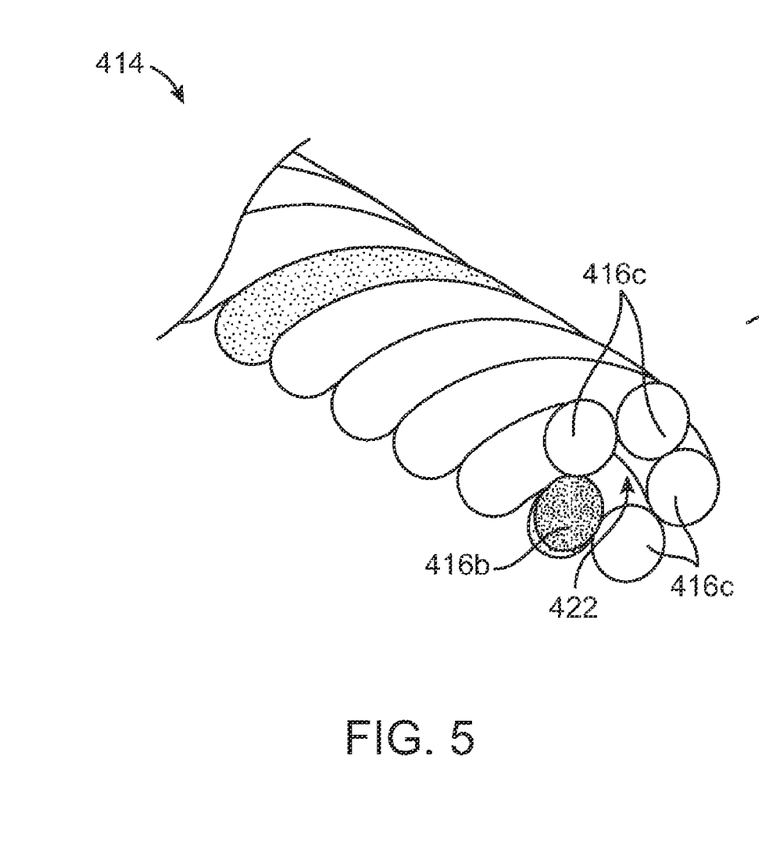
FIG. 5 schematically depicts a perspective view of the cable of FIG. 4 after a center strand has been removed.

FIG. 4 illustrates an embodiment of the cable 14, generally indicated by 414. The cable 414 includes six strands 416, including one strand 416a that is in the central core of the cable 414 when the cable is formed, and one strand 416b that comprises a bioerodable material, such as magnesium. The strands 416 may be twisted or braided together to form the cable 414, as generally illustrated in FIG. 5. The central strand 416a may comprise a material that is different from the bioerodable strand 416b and remaining strands 416c in that it is more easily plastically deformable. For example, the central strand 416a may comprise copper, while the remaining strands 416c may comprise MP35N cobalt alloy. In order to remove the central strand 416a to form a central cavity 422, the central strand 416a may be plastically deformed under a tensile load and removed from the remaining strands 416c and the bioerodable strand 416b. In an embodiment, the central strand 416a may comprise tantalum or any other suitable sacrificial metal that may be removed via a dry etch process. FIG. 5 illustrates the cable 414 after the central strand 416a has been removed to create the central cavity 422.

Figure 6:
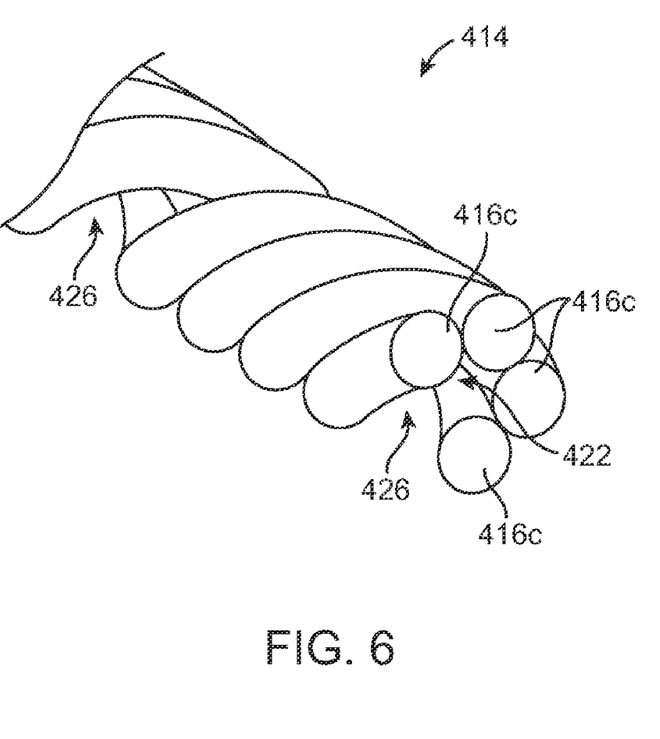
FIG. 6 schematically depicts the cable of FIG. 5 after a bioerodable strand has eroded.

The central cavity 422 may be at least partially filled with the therapeutic substance prior to implantation of the stent 10 into a body lumen. After implantation, the bioerodable strand 416b may erode so as to form a channel 426, as illustrated in FIG. 6, through which the therapeutic substance may exit the central cavity 422 and the stent 10. The remaining strands 416c may remain in the lumen to provide the luminal scaffolding as the stent 10 elutes the therapeutic substance. The bioerodable material may be selected to provide elution of the therapeutic substance within hours to days following implantation, as desired.

Figure 7:
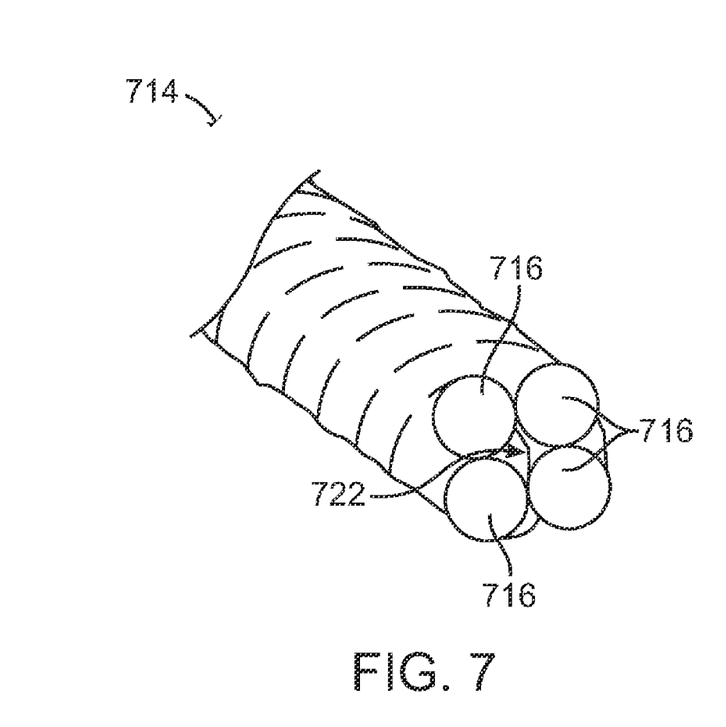
FIG. 7 schematically depicts a perspective view of an embodiment of the cable of FIG. 2.
Figure 8:
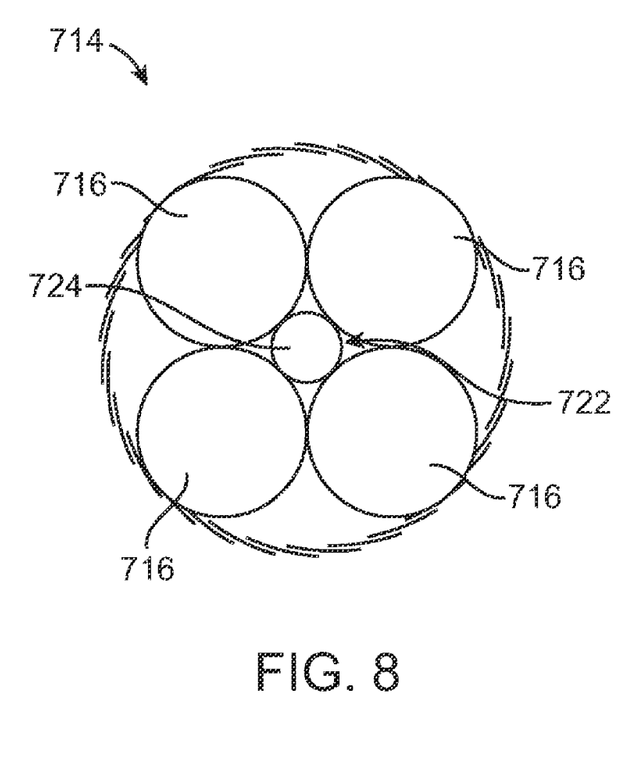
FIG. 8 schematically depicts a cross-section of the cable of FIG. 7 after a central cavity of the cable has been filled with a filler.
Figure 9:
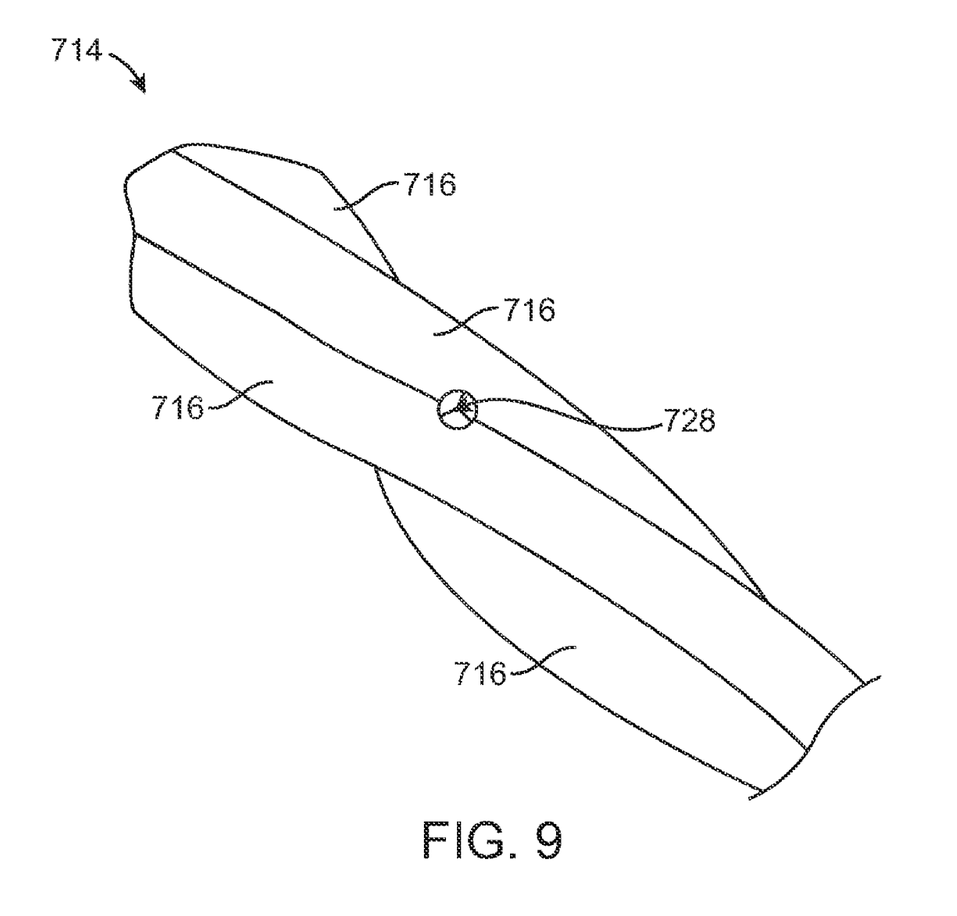
FIG. 9 schematically depicts a perspective view of the cable of FIG. 8 after an aperture in the cable has been formed.

FIGS. 7 and 8 illustrate an embodiment of a cable 714 that includes four strands 716 that have been braided together so as to form a central cavity 722 in the center of the strands 716. The central cavity 722 may then be at least partially filled with a filler 724 comprising the therapeutic substance, as illustrated in FIG. 8. Any suitable method may be used to at least partially fill the central cavity 722 with the filler 724. For example, the filler 724 may be injected into the central cavity 722 under positive pressure, or the filler 724 may enter the central cavity 722 under a vacuum environment. In an embodiment, the central cavity 722 may be filled after the stent 10 has been formed. At least one of the strands 716 may comprise a sacrificial material, such as tantalum, that may be removed via a dry etch process after the cable 722 has been formed. If the entire strand is removed, a channel like the channel 426 illustrated in FIG. 6 may be formed. As illustrated in FIG. 9, an aperture 728 may be formed through at least one of the strands 716 to allow for elution of the therapeutic substance from the central cavity 718 to the body lumen after the stent 10 has been implanted in the body lumen.

Figure 10:
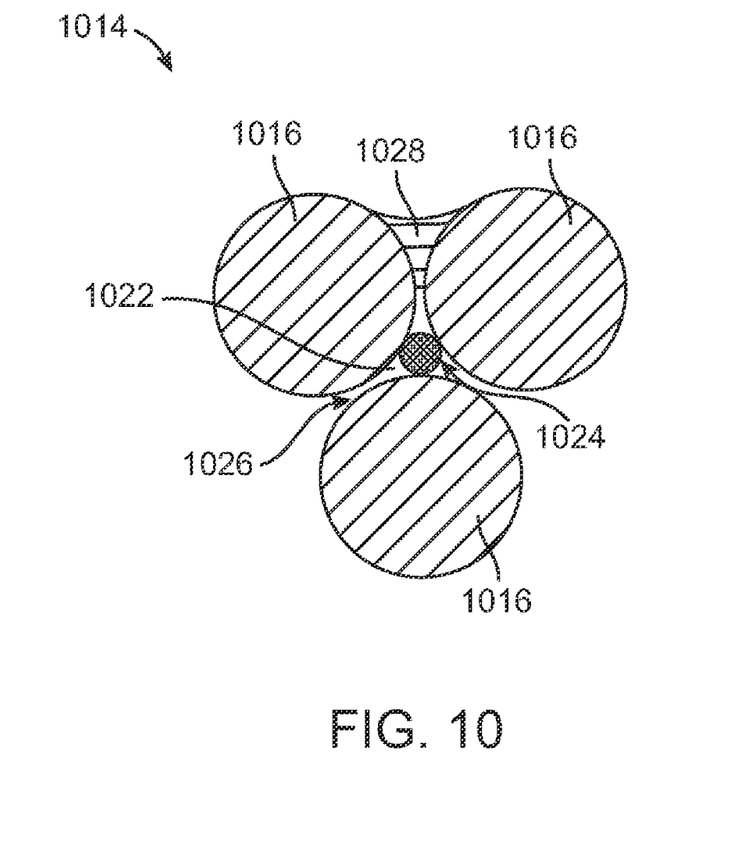
FIG. 10 schematically depicts a cross-section of an embodiment of the cable of FIG. 2.
Figure 11:
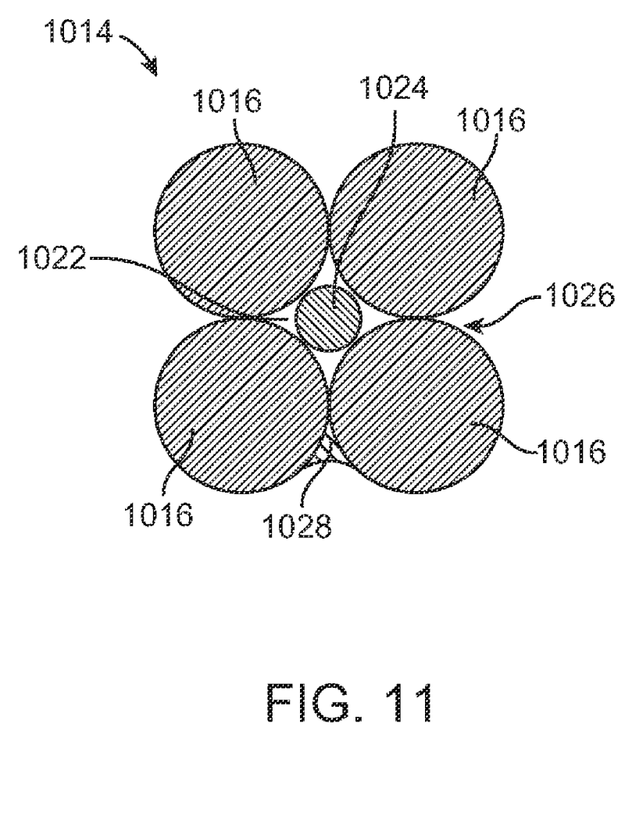
FIG. 11 schematically depicts a cross-section of an embodiment of the cable of FIG. 2.

FIGS. 10 and 11 illustrate embodiments of a cable 1014 that includes three and four strands 1016, respectively, that are wrapped around a filler 1024 so as to also form a central cavity 1022 in which the filler 1024 is positioned. The filler 1024 may include a drug impregnated core that may also be bioabsorbable. In an embodiment, the filler 1024 may also include materials that are radiopaque and/or stiff so as to provide the core with additional properties, as desired. A drug or therapeutic substance that is contained in the filler 1024 may elute out of the cable 1014 through gaps 1026 that are between the strands 1016. The size of the gaps 1026 may be controlled via winding tightness, the diameter of the strands 1016, the diameter of the filler 1024, etc. At least two of the strands 1016 may be connected with, for example, spot welds or adhesives 1028 (as illustrated in FIGS. 10 and 11). In an embodiment, the adhesive 1028 may be a continuous non-polymeric element or sealant that may create a seal or barrier to control elution. In one embodiment, the continuous non-polymeric element comprises a starch, cellulose or sugar configured to provide a predetermined elution rate or configured to dissolve in a predetermined length of time after implantation at the treatment site. The predetermined length of time may be less than one minute. In another embodiment, the predetermined length of time is between 60 seconds and one hour or between one hour and twenty-four hours. In another embodiment, the predetermined length of time is between one day and two weeks. The filler 1024 and/or the strands may be tailored to provide variable drug content, stiffness, elution rates, radiopacity, crossing profile, etc., as desired. Preferential radiopacity at the ends of the stent 10 may be achieved by varying the wind ratios of multiple filler cores, as desired.

Figure 12:
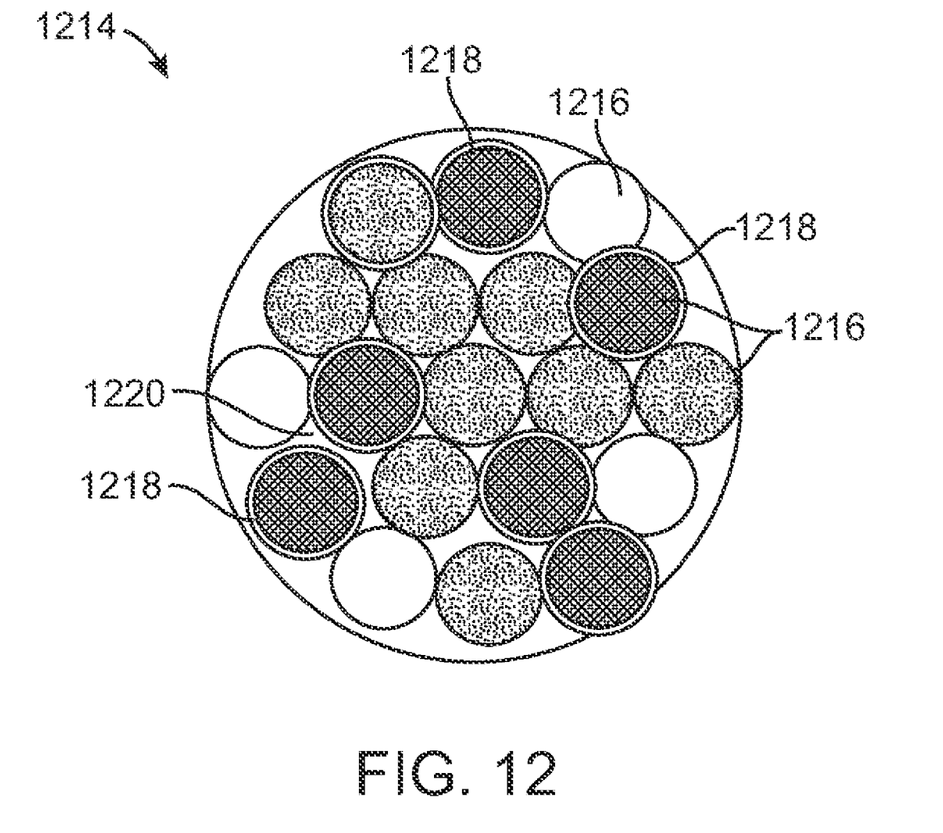
FIG. 12 schematically depicts a cross-section of an embodiment of the cable of FIG. 2.

FIG. 12 illustrates an embodiment of a cable 1214 that includes a plurality of strands 1216 that may be interwoven or braided to form the cable 1214. In an embodiment, individual strands 1216 may be made from different materials, such as stainless steel, MP35N cobalt alloy, Nitinol, platinum, magnesium, polymers, etc., to provide enhanced properties, such as radiopacity, flexibility, fatigue, etc., for the stent 10. In embodiments in which polymer strands are used, the polymer strands may be made of a bioerodable or bioabsorbable material that contains a therapeutic substance that may be released from the stent 10 when the polymer strands dissolve after implantation.

In an embodiment, the strands 1216 may be coated with therapeutic substances, as indicated by coating 1218 in FIG. 12, to increase the amount of therapeutic substances that may be delivered by the stent 10. The therapeutic substance may be applied to at least one of the strands 1216 by a suitable method, including, but not limited to, dipping, spraying, pad printing, inkjet printing, rolling, painting, micro-spraying, wiping, electrostatic deposition, vapor deposition, epitaxial growth, and combinations thereof. As just one example, the therapeutic substance may be contained in a gel that is sprayed onto the outer surface of the strand. Examples of therapeutic substances that may be used to coat the individual strands 1216 are described in further detail above. The gaps 1220 formed between the strands 1216 may be at least partially filled with the therapeutic substance, as illustrated in FIG. 12, either as part of a filler, described above, or by itself.

Returning to FIG. 1, after the cable 14, including any of the embodiments of cables 314, 414, 714, 1014, 1214 described above, has been formed and the wave form 12 has been formed, the wave form 12 may be wrapped around a mandrel, a center of which may define the longitudinal axis LA of the stent 10. The wave form 12 may be wrapped at an angle that is not perpendicular to the longitudinal axis LA to form a plurality of helical turns 22 that together generally form a helical coil in the shape of a helix.

The stent 10 also includes a plurality of connections 24 that are configured to connect selected crowns 20 of adjacent turns 22, as generally depicted in FIG. 1. The connections 24 may be created by fusing the selected crowns 20 together. As used herein, "fusing" is defined as heating the target portions of materials to be fused together, without adding any additional material, to a level where the material in the target portions flow together, intermix with one another, and form a fusion when the materials cool down to, for example, room temperature. A suitable laser may be used to create the fusion.

In an embodiment, the connections 24 may be created by welding or soldering the selected crowns 20 together. As used herein, "welding" and "soldering" are defined as heating an additional material that is separate from the selected crowns and applying the heated additional material to the selected crowns 20 so that when the additional material cools, the selected crowns 20 are welded or soldered together.

In an embodiment, the connections 24 may be created by fusing, welding, or soldering an additional piece of material (not shown) that extends between selected crowns 20. The additional piece of material may resemble a strut or a portion of a strut, and may be sized to provide spacing between the selected crowns of two adjacent turns, if desired. The illustrated embodiments are not intended to be limiting in any way.

Figure 13:
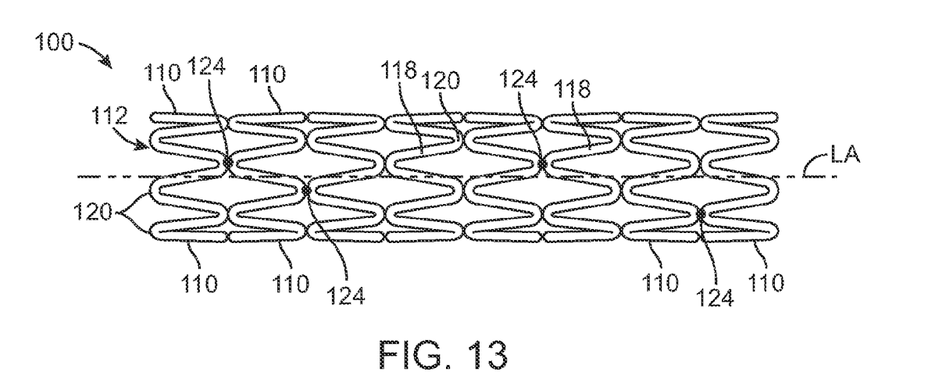
FIG. 13 schematically depicts a stent according to an embodiment of the present invention.
Figure 14:
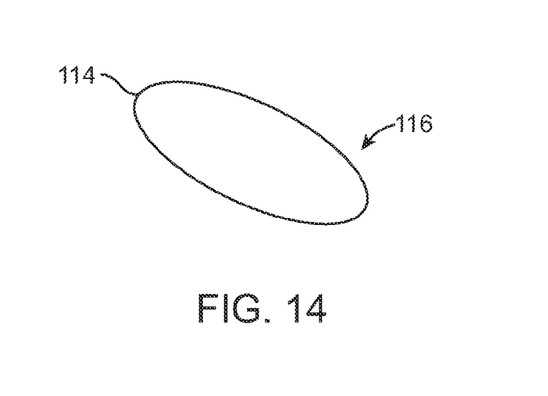
FIG. 14 schematically depicts the cable of embodiments of the invention formed into a ring.

FIG. 13 illustrates a stent 100 according to an embodiment of the invention. The stent 100 includes a plurality of ring-shaped elements 110, each of which includes a continuous wave form 112. The ring-shaped elements 110 are disposed substantially perpendicular to the longitudinal axis LA. Each ring-shaped element 110 may be formed from a cable 114 that is formed into a ring 116, as illustrated in FIG. 14, and then formed into the continuous wave form 112 by known methods. The cable 114 may be of any of the embodiments of cables 314, 414, 714, 1014, 1214 described above.

As illustrated in FIG. 13, each wave form 112 includes a plurality of struts 118 and a plurality of crowns 120. Each crown 120 is a curved portion or turn within the wave form 112 that connects adjacent struts 118 to define the continuous wave form 112. The struts 118 are substantially straight portions of the wave form 112. In other embodiments, the struts 118 may be slightly bent or have other shapes, such as a sinusoidal wave, for example. The illustrated embodiment is not intended to be limiting in any way.

The stent 110 also includes a plurality of connections 124 that are configured to connect selected crowns 120 of ring-shaped elements 110, as generally depicted in FIG. 13. The connections 124 may be created by fusing the selected crowns 120 together or welding the selected crowns 120 together, as described above with respect to the connections 24 of the stent 10 of FIG. 1.

Embodiments of the stents 10, 110 described herein may be balloon-expandable or may be self-expanding, and the materials used for the strands of the cables 314, 414, 714, 1014, 1214 may be selected accordingly. The stents 10, 110 may be bare metal stents, i.e., stents that do not have a coating, or the stents 10, 110 may have a sugar or cellulose coating the dissolves to bare metal after the stents 10, 110 have been inserted in the body lumen.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient roadmap for implementing an exemplary embodiment of the invention, it being understood that various changes may be made in the function and arrangement of members described in an exemplary embodiment without departing from the scope of the invention as set forth in the appended claims.

What is claimed is:

1. A stent comprising:
a wave form comprising a cable comprising a plurality of strands, the wave form having a plurality of struts and a plurality of crowns, each crown connecting two adjacent struts, the wave form being a continuous sinusoidal wave, the continuous sinusoidal wave wrapped around a longitudinal axis at a pitch to define a plurality of helical turns; and
a filler located within the cable, the filler comprising a therapeutic substance,
wherein the plurality of strands define a center cavity, and wherein the filler is located in the central cavity.

2. The stent according to claim 1, wherein at least one of the strands is bioerodable and is configured to form a channel communicated to the central cavity after the stent has been implanted in a body lumen.

3. The stent according to claim 1, further comprising an aperture extending through at least one of the strands to the center cavity.

4. A stent comprising:
a wave form comprising a cable comprising a plurality of strands, the wave form having a plurality of struts and a plurality of crowns, each crown connecting two adjacent struts, the wave form being a continuous sinusoidal wave, the continuous sinusoidal wave wrapped around a longitudinal axis at a pitch to define a plurality of helical turns; and a filler located within the cable, the filler comprising a therapeutic substance, wherein the strands are braided.

5. A stent comprising:

a wave form comprising a cable comprising a plurality of strands, the wave form having a plurality of struts and a plurality of crowns, each crown connecting two adjacent struts, the wave form being a continuous sinusoidal wave, the continuous sinusoidal wave wrapped around a longitudinal axis at a pitch to define a plurality of helical turns; and a filler located within the cable, the filler comprising a therapeutic substance, further comprising a weld or an adhesive configured to connect at least two of the strands.

* * * * *